United States Patent [19]

Chang et al.

[11] 4,423,199

[45] Dec. 27, 1983

[54] ACRYLAMIDE CONTAINING EMULSION COPOLYMERS FOR THICKENING PURPOSES

[75] Inventors: Ching-Jen Chang, Chalfont; Travis E. Stevens, Ambler, both of Pa.

[73] Assignee: Rohm and Haas Company, Philadelphia, Pa.

[21] Appl. No.: 431,880

[22] Filed: Sep. 30, 1982

[51] Int. Cl.³ .............................................. C08F 20/54
[52] U.S. Cl. ............................... 526/307.6; 524/553; 524/555; 526/305
[58] Field of Search ................. 526/305, 307.2, 307.6; 524/555, 812, 813, 553

[56] References Cited

U.S. PATENT DOCUMENTS

| | | | |
|---|---|---|---|
| 2,790,789 | 4/1957 | Miller | 526/305 |
| 3,451,982 | 6/1969 | Mortimer | 526/305 |
| 4,144,388 | 3/1979 | Yatsu | 526/305 |

*Primary Examiner*—Paul R. Michl
*Attorney, Agent, or Firm*—Alex R. Sluzas

[57] ABSTRACT

There are disclosed stable, aqueous dispersions of water-insoluble emulsion copolymers of (1) about 10–70% by weight of methacrylic or acrylic acid, (2) about 0.5–25% by weight of an N-alkyl acrylamide, and (3) at least 25% by weight, to a total of 100%, of a $C_1$–$C_4$ alkyl (meth)acrylate, and, optionally, included in the total monomer mixture a small amount of (4) about 0.05–1% by weight of a polyethylenically unsaturated monomer. The emulsion copolymers, when neutralized and solubilized by addition of an alkali, are high efficiency thickeners for aqueous systems and have improved tolerance to ionic or electrolyte content. Typical systems that can be thickened are paint latices, cosmetic preparations, food preparations, ionic detergents, dye pastes for textiles, pharmaceuticals, and oil well drilling muds. Surfactants enhance the thickening properties afforded by the copolymers.

22 Claims, No Drawings

ACRYLAMIDE CONTAINING EMULSION COPOLYMERS FOR THICKENING PURPOSES

BACKGROUND OF THE INVENTION

This invention relates to emulsion copolymers and their use for the thickening of a variety of aqueous systems, to methods of thickening utilizing the copolymers, to enhancement of such thickening by the addition of surfactants, and to other aspects including coating compositions and other aqueous systems thickened with the polymers.

This application is related to applicant's Ser. No. 101,615, filed Dec. 10, 1979, and corresponding to European Patent Publication No. 13,836, dated Aug. 6, 1980, entitled "(Meth)acrylic Acid Emulsion Copolymers for Thickening Purposes". This earlier application discloses emulsion copolymers, and the use thereof as thickeners in aqueous dispersions, of (meth)acrylic acid, an alkyl poly(oxyethylene) (meth)acrylate, and a $C_1$–$C_4$ alkyl (meth)acrylate, and, optionally, a small amount of a polyethylenically unsaturated monomer.

European Patent Publication No. 11,806, dated June 11, 1980, discloses aqueous emulsion polymers which are pH responsive and are prepared by emulsion polymerization of 15–60% of an $\alpha,\beta$-ethylenically unsaturated carboxylic acid, 15–80% of an $\alpha,\beta$-ethylenically unsaturated monomer, and 1–30% of a nonionic vinyl surfactant ester, preferably a monovinyl ester such as nonyl phenoxy poly(ethyleneoxy)$_9$ ethyl acrylate.

U.S. Pat. No. 4,138,381 discloses a liquid composition useful as a thickening agent in polymeric latices of (A) 50 weight percent of a polymer of units of (1) 10–98% of an unsaturated $C_3$–$C_6$ carboxylic acid, (2) about 1–50% of a $C_1$–$C_{30}$ alkyl (meth)acrylate, and (3) 1–18% of an ester of the formula:

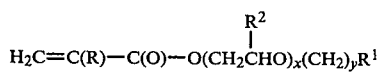

where x is 5–80, y is 0–20, R and $R^2$ are H or $CH_3$, and $R^1$ is alkyl or phenyl; and (B) as a solvent for (A), (4) a glycol, or (5) a glycol containing up to 50% of its weight of water; the composition being made by free radical solution polymerization techniques.

U.S. Pat. No. 4,268,631 discloses a normally solid, base-neutralized copolymer having copolymerized therein about 90–99 mole percent of a carboxyl-containing ethylenically unsaturated hydrocarbon and about 1–10 mole percent of a nonionic surfactant acrylate having the formula:

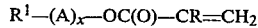

wherein R is H or $CH_3$, $R^1$ is a hydrophobe selected from the group consisting of alkyl—O—, alkyl—CH—, and alkyl—CO—, where alkyl contains 4–30 carbon atoms, A is a divalent radical selected from the group consisting of oxyethylene or oxyalkylene units or mixed oxyalkylene units $-(OC_nH_{2n})$-where n is an integer from 2 to 4 and x is an integer of 5–40, said surfactant acrylate having an HLB (hydrophilic lipophilic balance) value of about 10–19.

Salts of polyacrylic acid and polymethacrylic acid are well known as thickeners for various aqueous systems. A polyacrylic acid obtained by copolymerizing acrylic acid with a small amount (about 0.2 to 1% by weight on the weight of acrylic acid) of diallyl sucrose (U.S. Pat. No. 2,798,053) has also been sold for use as a thickener for many years. These thickening agents are difficult to handle because they are either powders that are slow to dissolve or very viscous aqueous solutions. Adverse effects such as stiffness or water sensitivity also may be imparted to the finished product by the polymeric acid thickener. Still another problem associated with the acid thickeners is their electrolyte sensitivity. The aqueous systems thickened with these thickeners decrease drastically in viscosity upon addition of an electrolyte, such as sodium chloride.

British Pat. No. 870,994 discloses the preparation of aqueous emulsion copolymers of methacrylic acid and a lower ($C_1$–$C_4$) alkyl acrylate which gives good thickening upon neutralization. The copolymer dispersions having a solids concentration of 25 to 50% by weight are low viscosity fluids and are thus readily added directly to systems to be thickened. However, they also have severe electrolyte sensitivity.

These polyelectrolyte polymers are useful as bodying and suspending agents in various mucilaginous and colloidal gel-like applications such as dentrifices, surgical jellies, creams and ointments, printing paste thickeners, and the like. However, most polyelectrolyte solutions decrease drastically in viscosity upon the addition of electrolytes such as sodium chloride. These prior art thickener materials are ion-sensitive and do not adequately maintain the viscosities of water or organic solvent solutions containing inorganic salts such as sodium chloride, even when a third monomer such as 2-ethylhexylacrylate or styrene, respectively, is included in the polymer as is suggested by the respective prior art patents.

DESCRIPTION OF THE INVENTION

In accordance with the present invention, novel N-alkyl acrylamides are used to produce stable aqueous dispersions of certain water-insoluble emulsion copolymers. The emulsion copolymers contain units from an addition polymerizable carboxylic acid, an N-alkyl acrylamide, and a copolymerizable comonomer, which are quite fluid at a pH below about 7 even though they have solids contents of 25 to 50% or even higher, but upon partial or substantial neutralization with ammonium hydroxide or an alkali metal hydroxide, such as sodium, potassium, or lithium hydroxide, or a volatile amine, such as triethylamine or triethanolamine, become highly viscous and are suitable for thickening aqueous media of a wide variety, using the same general procedure disclosed in the British patent mentioned above. As compared to the thickeners of the British patent, those copolymer thickeners of the present invention containing the polymerized units of N-alkyl acrylamides defined herein generally provide markedly greater viscosity at given levels, and have one or more advantages, such as less sensitivity to electrolyte content of the aqueous medium thickened; also improved flow and leveling when used as a rheology modifier in latex coating compositions such as water-base paints. In pigment printing pastes for coloring of textiles, the use of thickeners of the present invention is quite advantageous in respect to use of formulation, compatibility with a wide variety of pigment binders and pigment dispersions, high thickening efficiency resulting in brilliant coloration, good color yield and sharp demarcation, freedom from flushing and haloing, minimal stiffening of the printed area, resistance to crocking, to washing, to drycleaning, and to exposure to sunlight. In "all-aqueous" silk screen pigment printing systems, the thickeners of the present invention provide convenience of handling, good color depth, sharp mark detail with no haloing, and improved "holdout," i.e. less "strikethrough."

The novel and improved copolymers of the present invention are those obtainable by copolymerization of a monomer system comprising:
(1) at least about 10 weight percent of a monomer or a mixture of monomers selected from the group consisting of methacrylic acid, itaconic acid, acrylic acid, acryloxypropionic acid, fumaric acid, maleic acid, citraconic acid and crotonic acid;
(2) about 0.5 to 25 weight percent of at least one monomer of the formula:

$$H_2C=CH-C(O)-NH-R$$

wherein
R is selected from the group consisting of alkyl, alkylaryl, and polycyclic alkyl groups having 8 to 30 carbon atoms;
(3) optionally at least one copolymerizable ethylenically unsaturated monomer selected from the group consisting of compounds of the formula $$H_2C=CYZ$$

wherein:
(a) Y is H and Z is $COOR''$, $C_6H_4R'''$, CN, Cl, $CONH_2$, $OC(O)R'''$ or $CH=CH_2$;
(b) Y is $C_1-C_4$ alkyl and Z is $COOR''$, $C_6H_4R''''$, CN, $CONH_2$, or $CH=CH_2$; or
(c) Y and Z are Cl; and
  $R''$ is $C_1-C_8$ alkyl or $C_2-C_8$ hydroxyalkyl or lower alkoxy($C_2-C_8$)alklyl;
  $R'''$ is H, Cl, Br, or $C_1-C_4$ alkyl; and
  $R''''$ is $C_1-C_8$ alkyl; and
(4) zero to 1.0 weight percent of a polyethylenically unsaturated monomer.

Component (1) is preferably a polymerizable, monoethylenically unsaturated carboxylic acid selected from methacrylic acid, acrylic acid, itaconic acid and acryloxypropionic acid. More preferably, this component is methacrylic acid.

Component (3) is preferably a $C_1-C_4$ alkyl (meth)acrylate, more preferably ethyl acrylate, butyl acrylate, or methyl methacrylate, most preferably ethyl acrylate.

The copolymer can be an emulsion copolymer obtainable by copolymerization of the monomers in an aqueous inverse emulsion system, a solution polymer in an organic solvent, in water, or in compatible organic-aqueous solvents, a suspension copolymer, a normally solid copolymer or a non-aqueous dispersion (NAD) copolymer.

In a preferred embodiment, the novel and improved copolymers, and dispersions thereof, of the present invention are those obtainable by aqueous emulsion copolymerization of a monomer system comprising:
(1) about 10 to 70 weight percent of at least one member selected from the group consisting of methacrylic acid, acrylic acid, itaconic acid and acryloxypropionic acid; and
(2) about 0.5 to 25 weight percent of at least one monomer of the formula:

$$H_2C=CH-C(O)-NH-R$$

wherein
R is selected from the group consisting of alkyl, alkylaryl, and polycyclic alkyl groups having 8 to 30 carbon atoms;
(3) at least 30 weight percent of at least one copolymerizable ethylenically unsaturated monomer selected from the group consisting of compounds of the formula $$H_2C=CYZ$$

wherein
(a) Y is H and Z is $COOR''$, $C_6H_4R'''$, CN, Cl, $CONH_2$, $OC(O)R''''$ or $CH=CH_2$;
(b) Y is $C_1-C_4$ alkyl and Z is $COOR''$, $C_6H_4R''''$, CN, $CONH_2$, or $CH=CH_2$ or
(c) Y and Z are Cl;
  $R''$ is $C_1-C_8$ alkyl or $C_2-C_8$ hydroxyalkyl or lower alkoxy($C_2-C_8$)alkyl;
  $R'''$ is H, Cl, Br, or $C_1-C_4$ alkyl; and
  $R''''$ is $C_1-C_8$ alkyl; and
(4) zero to 1.0 weight percent of a polyethylenically unsaturated monomer;
the total of the percentages of monomers (1), (2), (3) and (4) being 100.

In general, the copolymers obtained have solids contents of from 25 to 50% by weight and the three-component copolymer (having components (1), (2) and (3) described above) dispersion has a weight average molecular weight of about 100,000 to several million. A chain-transfer agent may be used to obtain molecular weights in the lower part of the range or even down to about 8,000. On the other hand, use of 0.05% to about 1.0% of monomer component (4), based on total monomers, serves to provide molecular weights in or above the higher portion of the range mentioned.

The relative proportions of the first three components fall in the broad range of (1) 10–70 weight percent, (2) 0.5 to 25 weight percent, and (3) at least 25 weight percent, the total percentages of the three components being 100. The preferred ranges are (1) 30–45%, (2) 1–15%, and (3) 40–60%. In component (2) R is $C_8-C_{30}$, for example, lauryl ($C_{12}$), tridecyl ($C_{13}$), myristyl ($C_{14}$), or pentadecyl ($C_{15}$), more preferably $C_{10}$ to $C_{18}$ or mixtures thereof, examples being lauryl, myristyl, cetyl, and stearyl; longer chain alkyl groups, such as eicosyl ($C_{20}$), alkylaryl such as octyl-, nonyl- and dinonyl-phenyl, or polycyclic alkyl such as cholestanyl, lanostanyl, and abietyl. A mixture of several ($C_8-C_{30}$) alcohols to provide the R alkyl group in component (2) may be used.

In an especially preferred embodiment, the invention comprises a water-insoluble emulsion copolymer having the composition:
(1) about 30 to 45 weight percent of methacrylic acid;
(2) about 1 to 15 weight percent of at least one monomer of the formula:

$$H_2C=CH-C(O)-NH-R$$

wherein
R is an alkyl group having 10 to 18 carbon atoms and
(3) about 40 to 60 weight percent of ethyl acrylate.

The emulsion copolymers of the present invention may be produced by conventional aqueous emulsion polymerization techniques, using appropriate emulsifiers for emulsifying the monomer and for maintaining the polymer obtained in a stable, dispersed condition. Commonly used anionic surfactants such as sodium lauryl sulfate, dodecylbenzene sulfonate and ethoxylated fatty alcohol sulfate can be used as emulsifiers. The emulsifier may be used in a proportion of ½ to 6% of the weight of monomers.

Preferably, water-soluble initiators such as alkali metal or ammonium persulfate are used in amounts from 0.01 to 0.1% on the weight of monomers. A gradual addition thermal process employed at temperatures between 60° C. to 100° C. is preferred over redox systems for better incorporation of the hydrophobe-containing monomer (component (2)).

The polymerization system may contain small amounts (0.01 to 5% by weight, based on monomer weight) of the chain transfer agent mercaptans such as hydroxyethyl mercaptan, β-mercaptopropionic acid and alkyl mercaptans containing from about 4 to 22 carbon atoms. The use of mercaptan modifier reduces the molecular weight of the polymer and therefore its thickening efficiency. This may be desirable in certain areas of applications where proper rheology but not the thickening efficiency is of primary concern.

The copolymers hereinabove defined may be modified by introducing a small amount of component (4), namely, a polyethylenically unsaturated copolymerizable monomer effective for crosslinking, such as diallylphthalate, divinylbenzene, allyl methacrylate, or ethyleneglycol dimethacrylate. Thus, from 0.5 to 1.0% of such polyethylenically unsaturated compound based on total weight of monomer may be included in the composition forming the polymer. The resulting copolymers are either highly branched or in the form of three-dimensional networks. In the neutralized salt form, those networks swell in an aqueous system and the consequent "micro-gel" structure acts as a highly efficient thickener.

The copolymer may be utilized in a variety of ways to provide the thickener or thickened compositions of the invention. For example, the copolymer, while in aqueous dispersion or dry form, may be blended into an aqueous system to be thickened followed by addition of a neutralizing agent. Alternatively, the copolymer may first be neutralized in aqueous dispersion form and then blended with the aqueous system. Preferably, if cothickening by a surfactant is desired, the components are separately blended (as dry components or as dispersions or slurries) into an aqueous dispersion to be thickened, followed by the neutralization step. Although aqueous concentrates of the copolymer in acid form and the surfactant may be formed and added to an aqueous dispersion to be thickened as needed, followed by neutralization, such concentrates tend to be too viscous for easy handling. It is nevertheless possible to prepare either a dry blend or an aqueous, high solids composition which is sufficiently low in viscosity as to be pumpable or pourable, and then to further thicken the admixture by addition of an alkaline material.

The copolymer thickener may be provided in a dry state in a number of ways. For example, the unneutralized coplymer may be spray or drum dried and, if desired, blended with a surfactant cothickener. However, it is also possible to spray dry or otherwise dehydrate the neutralized copolymer thickener, and then reconstitute the aqueous thickener dispersion at a future time and place by agitation in an aqueous medium, provided the pH of the dispersion is maintained at pH 7 of higher.

The more usual method of application of the dispersion of the present invention for aqueous thickening is to add the aqueous dispersion of the carboxylic acid copolymer to the medium to be thickened and, after mixing, to introduce an alkaline material to neutralize the acid. The major portion of the thickening effect is obtained in a few minutes upon neutralization. In the presence of high concentrations of electrolytes, the viscosity development may take much longer. This method of applying a copolymer emulsion to an aqueous system before neutralization enables one to handle a high solids thickener in a non-viscous state, to obtain uniform blend, and then to convert to a highly viscous condition by the simple addition of an alkaline material to bring the pH of the system to 7 or above.

The aqueous solutions thickened with the neutralized latex copolymer of this invention exhibit good viscosity stability even at pH as high as 13.

The copolymer may be adapted to provide the thickener or thickened, at least partially neutralized, in acidic compositions in the presence of added surfactants wherein the thickened composition, for example, an aqueous system, has a pH below 7, even as low as 1.

The thickeners described here are useful in a variety of aqueous systems, such as textile printing pastes, latex paint formulations, cosmetic formulations, pigment dispersions, oil well drilling fluids, dentrifices, hand lotions, and liquid detergents.

SURFACTANT COTHICKENING

A remarkable enhancement of thickening (herein termed "cothickening") has been observed upon the addition of a surfactant to an aqueous system containing the emulsion copolymer of the invention, when the emulsion copolymer is neutralized. In some cases the thickening can be enhanced up to about 40 times the viscosity afforded by the neutralized copolymer alone. A wide range of surfactant type and amount is effective. Generally, the surfactant may be used in an amount of about 0.1 to 0.5 parts sufactant per part copolymer, same basis. Although trace amounts of surfactant may be residually present from the emulsion polymerization of the monomers comprising the emulsion copolymer (for example, whatever may remain of the about 1.5 weight percent surfactant on monomers), such amounts of surfactant are not believed to result in any measurable cothickening.

On the basis of an aqueous system containing about 0.1 to 5% by weight of copolymer solids, a useful amount of surfactant for optimum cothickening is about 0.1 to 1.0% by weight of the total system. As indicated, the amounts of copolymer and surfactant cothickener may vary widely, even outside these ranges, depending on copolymer and surfactant type and other components of the aqueous system to be thickened. However, it has been observed that the cothickening reaches a maximum as surfactant is added and then decreases. Hence, it may be uneconomical to employ surfactant in amounts outside the stated concentrations and copolymer/surfactant ratios, but this can be determined in a routine manner in each case.

The preferred method of application of the emulsion copolymer and the surfactant for aqueous thickening is to add in any sequence the copolymer and the surfactant to the medium to be thickened and, after mixing, to introduce an alkaline material to neutralize the acid.

This method of applying copolymer emulsion and surfactant to an aqueous system before neutralization enables one to handle a high solids thickener in a non-viscous state, to obtain a uniform blend, and then to convert to a highly viscous condition by the simple addition of an alkaline material to bring the pH of the system to 7 or above. However, the copolymer in the aqueous system may also be neutralized before addition of the surfactant.

The surfactants which may be used include nonionics and anionics, singly or in combination, the selection necessarily depending upon compatibility with other ingredients of the thickened or thickenable dispersions of the invention. Cationic and amphoteric surfactants may also be used provided they are compatible with the copolymer and other ingredients of the aqueous system, or are used in such small amounts as not to cause incompatibility.

Suitable anionic surfactants that may be used include the higher fatty alcohol sulfates such as the sodium or potassium salt of the sulfates of alcohols having from 8 to 18 carbon atoms, alkali metal salts or amine salts of high fatty acid having 8 to 18 carbon atoms, and sulfonated alkyl aryl compounds such as sodium dodecyl benzene sulfonate. Examples of nonionic surfactants include alkylphenoxypolyethoxyethanols having alkyl groups of about 7 to 18 carbon atoms and about 9 to 40 or more oxyethylene units such as octylphenoxypolyethoxyethanols, dodecylphenoxypolyethoxyethanols; ethylene oxide derivatives of long-chain carboxylic acids, such as lauric, myristic, palmitic, oleic; ethylene oxide condensates of long-chain alcohols such as lauryl or cetyl alcohol, and the like.

Examples of cationic surfactants include lauryl pyridinium chloride, octylbenzyltrimethylammonium chloride, dodecyltrimethylammonium chloride, condensates of primary fatty amines and ethylene oxide, and the like.

The foregoing and numerous other useful nonionic, anionic, cationic, and amphoteric surfactants are described in the literature, such as "McCutcheon's Detergents & Emulsifiers 1978 Annual, North America Edition," MC Publishing Company, Glen Rock, NJ 07452, U.S.A., incorporated herein by reference.

A water-in-oil clear concentrate may be prepared, for example, by dissolving 5 parts of a surfactant, such as sorbitan mono-oleate, in 30 parts by weight of mineral spirits (a hydrocarbon distillate cut having a flash point over 102° C.), then adding while stirring 58 parts of one of the emulsion polymers of the present invention, e.g., one of the copolymers in Table II below, at 30% solids and mixing therein 7 parts of 28% ammonium hydroxide to at least partially neutralize the polymer dispersion and thereby thicken it. The resulting composition may be useful as a clear concentrate that can be diluted with about 95 to 98 parts of water to form a printing clear. Such a clear can then be mixed with an aqueous emulsion polymer to serve as a binder, and, if desired, with a color concentrate. The commercial practice to date has been to prepare water-in-oil types of clear concentrates commonly used for the textile printing and dyeing industry by mixing a dusty, powdered thickener, such as certain dry products of U.S. Pat. No. 2,798,053 with other ingredients. The use of polycarboxylic acid thickeners in the form of aqueous emulsion polymer dispersions for preparation of printing compositions for the textile printing and dyeing industry, though suggested in the British patent (page 6, lines 58 to 70), has not been accepted commercially, presumably because of inadequate thickening efficiency obtained by the use of such emulsion polymer dispersions and/or the lack of reliable viscosity expectations in the event of adventitious presence of cations, such as sodium, calcium, magnesium, which may be present in hard water used or in the case of sodium, present in a softened water in an amount that varies in dependence upon unreliable deionization. The probability of adventitious occurrence of such cations, especially that of sodium, is particularly high in the commercially available pigment or color concentrates. The emulsion copolymers of the present invention are expected to provide a more efficient thickening effect and are less sensitive to the presence, adventitiously or otherwise, of such cations.

Pigment pastes may be prepared using various color concentrates from the printing clear obtained as described in the foregoing paragraph by the addition of a color concentrate, e.g., Aqua Hue Blue BGG 9521, and an aqueous emulsion copolymer binder in accordance with the following print paste code or chart:

| Print Paste Code | A | B | C | D |
|---|---|---|---|---|
| Printing Clear | 80 | 80 | 80 | 80 |
| Binder (35% Solids) | 10 | 10 | 10 | 10 |
| Color Concentrate | — | 0.6 | 3 | 10 |

The following commercially available colorants may be used in place of the Aqua Hue Blue BGG 9521, each of the following being used to produce printing pastes having color levels corresponding to B, C, and D:
1. Magenta W-5030
2. Aqua Hue Scarlet BYDC
3. Helizarine Red BN
4. Blue 3G Type W A dentrifice may be prepared using one of the polymers of Table II by mixing 1.7 parts of a 30% solids dispersion of the copolymer into a mixture of 20 parts sorbitol and 1.5 parts of sodium lauryl sulfate. Then 0.07 parts of sodium hydroxide is mixed in throughly to thicken the mixture and 50 parts of finely-divided calcium carbonate is mixed in water (about 27 parts) being mixed in gradually to form a uniform paste.

A hand lotion may be prepared by mixing 48.5 parts of glycerine with 1.7 parts of a 30% solids dispersion of copolymers of Table II, adding 0.5 parts triethanolamine while stirring and then adding about 50.5 parts of water gradually to form an unctuous liquid.

An all-purpose liquid detergent for household use may be made by mixing the following ingredients in the proportions (parts) and in the order specified in the table:

| | |
|---|---|
| Tetrapotassium pyrophosphate | 1.0 |
| 2-Butoxyethanol | 2.0 |
| TRITON ® X-100 [octylphenoxy (ethoxy)$_{9-10}$ ethanol] | 1.0 |
| Copolymer of Table II (30% solids) | 1.3 |
| NaOH | 0.2 |
| Water | 94.5 |

A "fracturing" fluid for stimulating the production of oil from oil-wells may simply be made up by mixing one part of a 25% to 30% solids dispersion of one of the polymers of the invention listed in Table II with about 0.04 part of NaOH and sufficient water to make a total of 100 parts.

A pigment dispersion for use in making a water-base paint employing aqueous emulsion vinyl addition polymers, e.g. of acrylic esters, vinyl acetate, styrene-butadiene, etc. as the primary binder, may be prepared by mixing a pigment, such as TiO₂, with a pigment dispersant, e.g. TAMOL® 731 or TAMOL® 850, with a copolymer dispersion of the present invention listed in Table II with water and neutralizing with a basic material, e.g. NH₃, NaOH, or triethylamine. A suitable formulation is the following, the parts of pigment, dispersant and thickening copolymer of the invention listed in Table II being based on solids.

| Ingredient | Parts |
| --- | --- |
| Pigment | 60.0 |
| Dispersant | 0.18 |
| Polymer (e.g. 30% solids) | 0.4 |
| NaOH | 0.06 |
| Water (to make 100) | -balance |

In the following examples illustrative of the invention, the parts and percentages are by weight and the temperatures are in Celsius degrees unless otherwise stated.

The following Example A is a suitable procedure for producing the N-alkyl acrylamides which constitute component (2) of the emulsion copolymer of the invention.

EXAMPLE A

Preparation of N-Alkyl Acrylamides

The branched N-alkyl acrylamides were prepared by the Ritter reaction following the procedure of T. Clarke et. al. (*J. Amer. Oil Chemists Soc.*, 41, 78, 1964). Thus, 168 g of 1-dodecene (1 mole) and 58.3 g of acrylonitrile (1.1 moles) were well stirred and cooled in a dry ice-acetone bath at temperatures between 0° to 25° C. while 400 g of concentrated sulfuric acid (98%, 4 moles) was added dropwise during 40 minutes. The mixture was then allowed to warm up to 30°–40° C. for one hour with continual stirring. Excess water was carefully added with further cooling, and the mixture was extracted with ether. The extract was washed with 100% sodium carbonate solution, dried, and evaporated. The residue was recystallized from acetone. The N-alkyl acrylamides prepared according to this procedure are summarized in Table I.

TABLE I

N—Alkyl Acrylamides
H₂C=CH—C(O)—NH—(R)

| Monomer No. | Olefin | N—Alkyl Acrylamide % Yield | MP° C. | R |
| --- | --- | --- | --- | --- |
| 1 | C₁₀H₂₀ | 89 | Slurry[1] | C₁₀H₂₁ |
| 2 | C₁₂H₂₄ | 92 | 61–63[2] | C₁₂H₂₄ |
| 3 | C₁₄H₂₈ | 92 | 48–51[1] | C₁₄H₂₉ |
| 4 | C₁₆H₃₂ | 62 | 65–67[2] | C₁₆H₃₃ |

[1]Crude product without crystallization
[2]After one recrystallization

EXAMPLE B

Preparation of Aqueous Emulsion Copolymers

An emulsion of monomers in water was preapred by adding 192.5 g of ethyl acrylate, 140 g of methacrylic acid, 17.5 g of N-decyl acrylamide (Monomer No. 1), 46.7 g of 30% solution of Alipal® EP-110 surfactant, and 433 g of water. To a reaction vessel containing 308 g of water at 90° C. was added 18.8% of the monomer emulsion and 55 g of 0.25% ammonium persulfate. After the initial charge had polymerized as evidenced by no refluxing at 90° C., the remaining monomer emulsion and 49.5 g of 0.5 ammonium persulfate were gradually added over a period of one hour. The temperature of the mixture was maintained at 86°–90° C. After completion of monomer and initiator feed, the mixture was held at 90° C. for 15 minutes and then 16 g of 0.87% ammonium persulfate solution was added and the mixture was then cooled and filtered. The filtrate gave an approximately 30% solids emulsion copolymer dispersion (essentially 100% yield) in which the copolymer composition is 5% N-decyl acrylamide, 55% ethyl acrylate, and 40% methacrylic acid.

In the following Table II, there are listed several representative copolymers which constitute aqueous emulsion copolymer dispersion thickener compositions according to the invention.

| Polymer | Monomers | Weight Ratio % | Viscosity[1], 1% |
| --- | --- | --- | --- |
| A | #1/EA/MMA | 5/55/40 | 50 |
| B | #2/EA/MAA | 5/55/40 | 150 |
| C | #3/EA/MAA | 5/55/40 | 250 |
| D | #4/EA/MAA | 5/55/40 | 9,100 |

[1]Brookfield viscosity at 12 rpm, solution neutralized with one equivalent of NaOH.

What is claimed is:

1. A copolymer polymerized from a monomer system comprising
   (1) at least about 10 weight percent of a monomer or a mixture of monomers selected from the group consisting of methacrylic acid, itaconic acid, acrylic acid, acryloxypropionic acid, fumaric acid, maleic acid, citraconic acid and crotonic acid;
   (2) about 0.5 to 25 weight percent of at least one monomer of the formula:

$H_2C=CH-C(O)-NH-R$ wherein:
   R is selected from the group consisting of alkyl, alkylaryl, and polycyclic alkyl groups having 8 to 30 carbon atoms;
   (3) optionally at least one copolymerizable ethylenically unsaturated monomer selected from the group consisting of compounds of the formula $H_2C=CYZ$ wherein
   (a) Y is H and Z is COOR″, C₆H₄R‴, CN, Cl, CONH₂, OC(O)R″″ or CH=CH₂;
   (b) Y is C₁–C₄ alkyl and Z is COOR″, C₆H₄R″″, CN, CONH₂, or CH=CH₂; or
   (c) Y and Z are Cl; and
   R″ is C₁–C₈ alkyl or C₂–C₈ hydroxyalkyl or lower alkoxy(C₂–C₈)alkyl;
   R‴ is H, Cl, Br, or C₁–C₄ alkyl; and
   R″″ is C₁–C₈ alkyl; and
   (4) zero to 1.0 weight percent of a polyethylenically unsaturated monomer.

2. A water-insoluble emulsion copolymer according to claim 1 polymerized from a monomer system comprising
   (1) about 10 to 70 weight percent of at least one member selected from the group consisting of methacrylic acid, acrylic acid, itaconic acid and acryloxypropionic acid; and
(2) about 0.5 to 25 weight percent of at least one monomer of the formula:

$H_2C=CH-C(O)-NH-R$ wherein:
R is selected from the group consisting of alkyl, alkylaryl, and polycyclic alkyl groups having 8 to 30 carbon atoms;
(3) at least 30 weight percent of at least one copolymerizable ethylenically unsaturated monomer selected from the group consisting of compounds of the formula $H_2C=CYZ$ wherein:
(a) Y is H and Z is COOR″, $C_6H_4R'''$, CN, Cl, $CONH_2$, OC(O)R″″ or $CH=CH_2$;
(b) Y is $C_1-C_4$ alkyl and Z is COOR″, $C_6H_4R''''$, CN, $CONH_2$, or $CH=CH_2$ or
(c) Y and Z are Cl and
R″ is $C_1-C_8$ alkyl or $C_2-C_8$ hydroxyalkyl or lower alkoxy($C_2-C_8$)alkyl;
R‴ is H, Cl, Br, or $C_1-C_4$ alkyl; and
R″″ is $C_1-C_8$ alkyl; and
(4) zero to 1.0 weight percent of a polyethylenically unsaturated monomer;
the total of the percentages of monomers (1), (2), (3) and (4) being 100.

3. A water-insoluble emulsion copolymer according to claim 2 polymerized from a monomer system consisting essentially of:
(1) about 10 to 70 weight percent of at least one member selected from the group consisting of methacrylic acid, acrylic acid, acryloxypropionic acid and itaconic acid;
(2) about 0.5 to 25 weight percent of at least one monomer of the formula;

$H_2C=CH-C(O)-NH-R$ wherein
R is selected from the group consisting of alkyl, alkylaryl and polycyclic alkyl groups having 8 to 30 carbon atoms;
(3) at least 30 weight percent of at least one alkyl (meth)acrylate in which the alkyl group has 1 to 4 carbon atoms; and
(4) zero to 1.0 weight percent of a polyethylenically unsaturated monomer;
the total of the percentages of monomers (1), (2), (3), and (4) being 100.

4. An aqueous dispersion of a copolymer according to claim 3 in which the proportion of component (1) is from 30 to 45 weight percent, the proportion of component (2) is from 1 to 15 weight percent, and the proportion of component (3) is about 40 to 60 weight percent.

5. An aqueous dispersion of a copolymer according to claim 3 in which R of component (2) is an alkyl group having 10 to 18 carbon atoms.

6. A water-insoluble emulsion copolymer according to claim 3 having the composition:
(1) about 30 to 45 weight percent of methacrylic acid;
(2) about 1 to 15 weight percent of at least one monomer of the formula:

$H_2C=CH-C(O)-NH-R$ wherein
R is an alkyl group having 10 to 18 carbon atoms.
(3) about 40 to 60 weight percent of ethyl acrylate.

7. An aqueous dispersion of an emulsion copolymer according to claim 2 which upon at least partial neutralization of the copolymer provides increased viscosity.

8. An aqueous dispersion of an emulsion copolymer according to claim 2 adapted to be formulated with an aqueous pigment dispersion and an aqueous dispersion of a vinyl addition emulsion polymer binder for making water-base paints containing the pigment in a pigment volume concentration of up to 65%, said aqueous dispersion of an emulsion copolymer according to claim 2 providing controlled rheological properties to the water-base paint upon at least partial neutralization of the emulsion copolymer according to claim 2.

9. An aqueous dispersion of an emulsion copolymer of claim 2 and a surfactant, said surfactant being present in an amount effective to thicken the dispersion beyond the thickening provided by at least partial neutralization of said emulsion copolymer.

10. The aqueous dispersion of claim 9 wherein the surfactant is anionic or nonionic.

11. A process of thickening an aqueous system, comprising adding to the system an emulsion copolymer according to claim 2 and at least partially neutralizing said copolymer.

12. A process according to claim 11 wherein the system is thickened further by the addition of an effective amount of surfactant.

13. A latex paint containing the neutralized composition made by the process of claim 11.

14. A pigment dispersion comprising the neutralized composition made by the process of claim 11.

15. An oil well drilling fluid comprising the neutralized composition made by the process of claim 11.

16. A textile printing paste comprising the neutralized composition made by the process of claim 11.

17. A dentrifice containing the neutralized composition made by the process of claim 11.

18. A hand lotion containing the neutralized composition made by the process of claim 11.

19. A liquid detergent comprising the neutralized composition made by the process of claim 11.

20. A water-base paint comprising an aqueous dispersion of a vinyl addition emulsion polymer binder selected from vinyl acetate polymers, polymers of esters of acrylic acid, polymers of esters of methacrylic acid, and styrene-butadiene polymers, said paint containing a pigment having a PVC up to 65%, and containing at least partially neutralized emulsion copolymers according to claim 2 to control the rheological properties of the paint.

21. A textile printing composition comprising a water-in-oil clear concentrate containing a surfactant, such as sortitan mono-oleate, dissolved in a hydrocarbon distillate, such as mineral spirits having a flash point over 120° C., and an aqueous dispersion of an emulsion copolymer of (meth)acrylic acid according to claim 2 mixed therewith to emulsify the water thereof in the hydrocarbon solution, the copolymer of claim 2 being then thickened by at least partial neutralization by a base, such as ammonium hydroxide, the resulting concentrate being dilutable with water to form a printing clear which can be mixed with an aqueous vinyl addition emulsion polymer to serve as binder, and optionally with a color concentrate to form a pigment paste for pigment printing, and dyeing of textiles.

22. A textile printing composition comprising a water-in-oil clear concentrate according to claim 21, additional water, an aqueous dispersion of a binder comprising a vinyl addition emulsion polymer having a heat-reactive component therein, and a color concentrate, the several components being mixed to form a pigment paste having desired rheological properties suitable for the pigment printing and dyeing of textiles.

* * * * *